(12) United States Patent
Eck et al.

(10) Patent No.: US 8,843,215 B2
(45) Date of Patent: Sep. 23, 2014

(54) CONNECTING DEVICE

(71) Applicant: Biotronik SE & Co. KG, Berlin (DE)

(72) Inventors: Stefan Eck, Hoechstadt (DE); Michael Arnold, Erlangen (DE); Thomas Flierl, Heroldsberg (DE); Peter Meidlein, Nuremberg (DE); Manuela Koehler, Berlin (DE); Christiane Podszuck, Fuerth (DE); Erich Haas, Flachslanden (DE); Josef Teske, Hallstadt (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 13/915,297

(22) Filed: Jun. 11, 2013

(65) Prior Publication Data

US 2013/0338750 A1    Dec. 19, 2013

(30) Foreign Application Priority Data

Jun. 13, 2012  (DE) .......................... 10 2012 209 872

(51) Int. Cl.
*A61N 1/00* (2006.01)
*A61N 1/375* (2006.01)
*A61N 1/362* (2006.01)
*A61N 1/372* (2006.01)

(52) U.S. Cl.
CPC .............. *A61N 1/362* (2013.01); *A61N 1/3754* (2013.01); *A61N 1/37229* (2013.01)
USPC ......................................................... 607/119

(58) Field of Classification Search
USPC ......................................................... 607/119
See application file for complete search history.

(56) References Cited

U.S. PATENT DOCUMENTS

2005/0007718 A1 *   1/2005   Stevenson et al. ............ 361/118
2011/0015694 A1 *   1/2011   Alexander et al. ............. 607/36

FOREIGN PATENT DOCUMENTS

DE    10 2009 035 972    4/2011
EP         1 897 588     3/2008

* cited by examiner

*Primary Examiner* — Robert N Wieland
(74) *Attorney, Agent, or Firm* — Buchanan Ingersoll & Rooney PC

(57) ABSTRACT

A connecting device for an electromedical implant having a housing, the connecting device including a feedthrough and a header. The feedthrough and the header are formed in one piece so as to reduce the cost of the production process.

20 Claims, 6 Drawing Sheets

CONNECTING DEVICE

CROSS-REFERENCE TO RELATED APPLICATIONS

This patent application claims the priority of German Patent Application No. DE 10 2012 209 872.0, filed on Jun. 13, 2012 in the German Patent Office, which is hereby incorporated by reference in its entirety.

TECHNICAL FIELD

The present invention relates to a connecting device for an electromedical implant having a housing, wherein the connecting device comprises a feedthrough and a header, and also to a corresponding electromedical implant.

BACKGROUND

A wide range of medical implants are known from the prior art. In conjunction with the present invention, an electromedical implant is understood to be an implant that, besides including a power supply (for example a battery), comprises further electrical and/or electronic components (for example, capacitors, etc.), which are arranged in a housing that is hermetically sealed. Electromedical implants of this type generally include cardiac pacemakers, defibrillators, neurostimulators, leadless pacemakers, cochlear implants or other hermetically encapsulated electronic products, for example.

Implants of this type are often connected to electrode lines, which treat a body after implantation therein, for example, transfer and/or deliver stimulation impulses and/or defibrillator shocks to specific points of the body, or are used to detect electronic potentials of points of the body. For this purpose, an electrical connection has to be produced between the electrical and/or electronic components arranged in the interior of the housing and the electrode line. This electrical connection is generally produced by means of a feedthrough and what is known as a header. A feedthrough is used in this instance to provide at least one electrical connection between the interior of the housing and the exterior environment, and is simultaneously responsible for the hermetic sealing of the housing. The header, fastened via the feedthrough, continues the electrical connection of the feedthrough to a contact point and is used to plug the at least one electrode line into a corresponding, generally standardized socket. Electrical contact between the implant and the connecting piece of the electrode line is thus produced at the contact points of the socket. Alternatively, an electrode line with an electrode may already be integrated into the header.

Ceramic feedthroughs are already known from the prior art, for example, from document European Patent No. EP 1 897 588 B1. With feedthroughs of this type, local metal coatings on ceramics are necessary for the soldering of feedthrough pins and of flanges. The metal solders form menisci and, therefore, the pins cannot be packed very densely due to the necessary insulation paths. It is also disadvantageous that ceramic feedthroughs and headers are joined in separate manufacturing steps to the implant housing and the electrical connections between the feedthroughs and electrical connecting points in the header have to be linked. Electromechanical connecting points or sockets for electrode lines have to be provided by means of plastic headers inclusive of individual metal components, such as, for example, sleeves, strips, etc. When using EMI filters with such a feedthrough, complex joining processes leading to high costs and errors (e.g., soft soldering, adhesive bonding, welding) are used in order to attach EMI filters to feedthroughs. To this end, additional components (e.g., capacitors) that are costly in terms of space are also necessary, inter alia at the feedthroughs themselves or at the connecting strips in the interior of the implant.

The same is also true of the glass feedthroughs or glass/ceramic feedthroughs already known, wherein, with some material combinations of the glass feedthroughs, it is additionally difficult to control the glass solder flux. With both types of feedthrough there are restrictions in terms of the feasible geometry and the selection of the materials due to the generally high soldering temperature and the accompanying coefficients of thermal expansion.

Feedthroughs are known from document German Patent No. DE 10 2009 035 972 A1, which has a collar-like retaining element, an insulation element, and at least one elongate line element. The line element is used to produce the electrical connection between the interior of the housing and the exterior of the implant. The line element of the known feedthrough is characterized in that it has a cermet, that is to say a composite material, formed from ceramic materials in a metal matrix. With this known feedthrough also, the feedthrough and header each have to be produced and joined to the implant housing in separate manufacturing steps, and the electrical connections have to be linked. In the case of a feedthrough, the electrical connection to the adjacent elements is generally produced by pins, that is to say by protruding portions of the line elements. Cermet pins or feedthroughs are brittle, however, and therefore protruding connections may break easily, for example. Cermet pins protruding in a pin like manner, as are disclosed in the above cited document, are considered to be brittle, mechanically unstable connections. Furthermore, with the known feedthrough, the connected flanges of the retaining element are to be turned/milled, which is very complex. In addition, separate cermet pins, in particular running in a straight line, spare space in these feedthroughs. The construction of the known feedthroughs also causes mechanical stress peaks, and there is a potential risk of incorrect functioning of the implant as a result of unfiltered cermet feedthroughs. There is also a risk that the electrical insulation paths in the dense cermet pin arrangement will be too short and that an unsecure connection between the flange/cermet/insulation ceramic will result due to different coefficients of thermal expansion or that it will be impossible to produce the connection due to a necessary high sintering temperature, in particular with use of a "pure" $Al_2O_3$ ceramic having degrees of purity of more than 95%, for example, in the cermet feedthrough.

An additional cost is also necessary with use of the above disclosed feedthrough forms, and there is a risk of error during production, connection/activation and implantation of plastic headers. Further, with use of plastic headers, the reference and anchor points have to be joined on (generally welded on) to implant housings in a separate process with additional spatial requirement.

The present invention is directed toward overcoming one or more of the above-identified problems.

An object is therefore to create a connecting device that can be produced in a simple and, therefore, cost-effective manner. A further object is to create a corresponding electromedical implant.

SUMMARY

At least the above objects are achieved by a connecting device having the features of the claims.

In accordance with the present invention, the feedthrough and the header, in particular, are formed in one piece. Alternatively, or in addition, the connecting device according to the present invention has a supporting body made of insulating material, as well as at least one electrically conductive pathway, which, at its first end and/or its second end, has at least one contact point for transferring electrical signals between a circuit arranged in the housing and an electrode line, wherein the pathway contains a cermet material, and preferably consists of a cermet material.

In accordance with the present invention, a connecting device therefore comprises merely a single unit, which contains the feedthrough and the header, as well as cermet feedthroughs, which are already integrated in the header and pass through the entire connecting device, that is to say the feedthrough and the header. The feedthrough preferably forms a first portion of the connecting device and the header forms a second portion of the connecting device, wherein the housing is particularly preferably hermetically sealed by means of the first portion. Electrical cermet lines, which are preferably angled, guide the electrical signals from cermet connecting points, which are located in the interior of the implant, to matched connecting points or sockets of cermet design, to which electrode lines can be connected using standard plug connectors. Due to the omission, according to the present invention, of separate ceramic feedthroughs in headers, as well as the omission of metal coatings on insulation ceramics, electrically conductive solder menisci can be avoided and a spatially more compact design can be obtained. Furthermore, electrically mechanical connecting points or sockets for electrode lines can be provided without additional components and manufacturing processes.

In conjunction with the present invention, cermet is understood to be a material that is electrically conductive. Furthermore, a cermet (a combination of the words 'ceramic' and 'metal') is a composite material formed from ceramic materials in a metal matrix. Cermets are characterized by a particularly high level of hardness and resistance to wear. The ceramic components are often aluminum oxide ($Al_2O_3$) and zirconium dioxide ($ZrO_2$), whereas platinum, iridium, niobium, tantalum, molybdenum, titanium, cobalt, zirconium, chromium and other metals or metal alloys are possible metal components. The significantly varying density between the metal and ceramic sinter components easily leads to demixing and, therefore, additional stabilizing materials are often provided in the cermet.

The solution according to the present invention signifies an omission of separate glass or ceramic feedthroughs in headers, the avoidance of a solder or control of the solder, and the abolishment or reduction of geometrical and material restrictions with regard to glass/ceramic feedthroughs.

Compared to the known cermet feedthroughs, the number of process steps until manufacture of the electromedical implant is considerably reduced, since there is no separate production of the header. Ductile electrical feedthroughs or connections may additionally be produced. In particular, the instability of brittle, mechanically unstable connections is reduced and the design is made more compact.

Conventional plastic headers are additionally mechanically fixed to implant housings via what are known as anchors or pins. These anchors are omitted with use of the connecting device according to the present invention.

In a preferred exemplary embodiment, a contact pin, a contact pad or a first socket is formed in the supporting body at the first end of the at least one pathway, and a second socket is formed in the supporting body at the second end of the respective pathway, wherein the second socket is used to plug in a corresponding connecting piece of the electrode line. In this exemplary embodiment, no, or few, additional components are required at the connecting strips in the interior of the housing. In a variant of the present invention, solid metal pins may be connected to the cermet pathway, said pins forming planar or recessed connecting faces with the supporting body, which is made of insulating material (for example, the insulation ceramic). Metal pins are flexible and do not break under flexural load to the extent of pins made of cermet.

In a development of the present invention, the first end and/or the second end of the at least one pathway is designed in the form of at least one hollow cylinder casing portion or a hollow cylinder casing or a flange portion, wherein the inner face of the hollow cylinder casing portion or of the hollow cylinder casing or of the flange portion of the pathway is used as a contact point of the respective first or second sockets. This variant includes a particularly simple possibility for producing a contact point between the cermet pathway and the connecting piece of the electrode line.

It is also advantageous if the material of the pathway at the first end and/or the second end of the at least one pathway is different from the material of the pathway in the intermediate portion, preferably has a greater concentration of metals and/or metal alloys than in the intermediate portion, and is particularly preferably composed of at least one metal or metal alloy. Multi-phase cermet junctions and alloys are therefore produced in the cermet. Furthermore, the ceramic porosity in the cermet can be reduced, in particular, at the first and second ends of the pathway by adding a material or a plurality of materials from the group containing MgO, metals, metal alloys and glass. In principle, different ceramic/metal mixtures can be used in the regions of the ends of the pathway so as to improve the conductive properties of the pathway and the contact to the connecting piece of the electrode line by means of a lower contact resistance.

Suitably shaped supporting body (parts) are more preferably used for production of a connecting device of this type, and ceramic housing half-shells can particularly preferably be used as supporting bodies with a cermet edge, which can be (laser) welded or soldered, possibly with a metal termination.

In accordance with a preferred exemplary embodiment of the present invention, the supporting body also has a volume area in the entry region of a socket, said volume area containing a cermet material to increase the mechanical stability.

In a further exemplary embodiment, an antenna may be arranged in the supporting body and preferably contains a cermet material, and more preferably has a thickening at one of its ends. Antennas of this type allow communication with the implant, for example, in the form of integrated loop or rod antennas. Due to the use of a one-piece connecting device comprising a cermet header and a cermet feedthrough, there is no need for separate electrical feedthroughs in the implant housing.

To hermetically seal the housing, the connecting device according to the present invention has a preferably peripheral flange in a particularly preferred exemplary embodiment, said flange particularly preferably containing a cermet material. A flange of this type can also be produced in a simple and cost-effective manner.

It is more preferable if the connecting device according to the present invention additionally comprises an EMI filter or, preferably in the region of the first end of the at least one pathway, is connected to such an EMI filter. In particular, in the event of integration into the connecting device, these filters cost-effectively lead to suppression of radio interference, since the additional connection of a separate anti-interference capacitor is omitted. In this case, an increased capacitor capacitance and filter effect can be achieved by the integration of special dielectrics or electrically non-conductive cermets between the (cermet) capacitor plates. Electrically non-conductive phases can be produced by low concentrations of metal particles in the supporting body and/or by integration of particles of higher permittivity in the supporting body, at least in the space between the capacitor plates. Cermet capacitor plates can accordingly be formed with staggered cermet phases with different metal fractions. The cermet capacitor plates can be connected in this case to cermet pins or cermet layers.

A further spatial reduction can be achieved by forming the at least one pathway in the intermediate portion in an L-shaped manner. The electrical insulation paths are additionally extended.

It is preferable, in particular, for the connecting device to be produced or producible by means of multi-layer technology. With this technology, a plurality of layers of green compact are used, wherein each layer consists either of one or more ceramic phases or a cermet. These layers are arranged selectively, for example, one above the other or side-by-side, such that fixedly connected, hermetically tight, three-dimensional structures containing electrically conductive cermet phases and electrically insulating ceramic phases, which can be arranged in one another, are produced once these layers have been sintered.

In terms of "leadless pacemakers", in the embodiment with a cermet electrode with and without electrode line directly at the cermet header, or with a ductile metal electrode attached directly to the cermet header, the electrode surface may additionally have a fractal coating so as to reduce the impedance between the electrode and the muscular cells of the heart.

In a further exemplary embodiment, cermet pins are used in the connecting device according to the present invention, which have thicker cross-sections at their ends compared to the cermet pathways, such that a facilitated and more reliable electrical and/or mechanical connection is enabled. Cermet pins that terminate in a planar and flush manner with the ceramic surrounding them so that breakage of the pins is avoided are also used.

The connection of a contact pad (for example, containing platinum, gold, silver, copper or alloys thereof) to a cermet surface can be implemented, for example, by means of screen printing, by means of hard soldering (suitable for silver or silver alloys), soft soldering, (resistance, laser, friction) welding, bonding, etc.

It is also advantageous if "MiM flanges" are used. Flanges of this type are produced cost-effectively by means of metal-powder injection moulding and not by complex non-cutting methods (for example, by turning or milling), as is the case in the prior art.

In a further exemplary embodiment, cermet pins having various diameters or a different metal fraction are used. This is advantageous since different electrical properties are required depending on pin configuration, that is to say depending on the function of the pin. For example, increased electrical conductivity is required for defibrillation or the signal line, which is achieved by a higher metal fraction in the cermet or by a greater cermet line cross-section. By contrast, sensor pathways with a lower requirement of current-bearing capacity can be formed more thinly, thus saving more space.

Conventional ceramic feedthroughs require metal coatings on their ceramic lateral surfaces so as to enable wetting with hard solder (for example, gold solder) and therefore so as to be able to solder on flanges. In accordance with a further exemplary embodiment of the present invention, this metal coating is replaced by a (preferably thin) cermet layer, which can be produced, for example, by means of the above-described multi-layer technique so that there is no need for a separate coating process.

It is further advantageous if at least one intermediate cermet phase with metal concentrations increasing in steps is provided to reduce the mechanical stress peaks or to avoid "hard" cermet ceramic junctions, said intermediate cermet phase not necessarily having to be electrically conductive. Instead of changing the metal concentrations, "gentle" low stress junctions can be created by using additional materials, such as, MgO, $ZrO_2$, glass, etc.

In a further exemplary embodiment, flanges are sintered on directly in the cermet sintering process, such that there is no need for a separately necessary connection process, such as high-temperature soldering, or prior coating of the ceramic.

A change to the coefficients of thermal expansion and/or the sintering temperature of the cermet material, which may be of significance for the production process or application, can be achieved by variation of the additional materials, such as, MgO, $ZrO_2$, glass, etc.

When using ceramic housing half shells, these can be joined in an improved and more reliable manner if ceramic housing half shells with a cermet edge, which can be (laser) welded, are used, possibly with a metal termination.

The above object is also achieved by an electromedical implant comprising a housing, a battery and an electric circuit as well as an above-described connecting device, wherein the circuit and the connecting device are preferably formed in one piece and the connecting device particularly preferably hermetically seals the housing of the medical implant. Further costs during production of the implant can be saved, in particular, with the one-piece design of the above-described connecting device and the circuit.

The connecting device according to the present invention and the electromedical implant according to the present invention will be explained hereinafter on the basis of the figures. All features illustrated and/or described form the subject of the present invention, independently of their summary in the claims or the references of the claims to other claims.

Further features, aspects, objects, advantages, and possible applications of the present invention will become apparent from a study of the exemplary embodiments and examples described below, in combination with the figures, and the appended claims.

DETAILED DESCRIPTION

Figure 1:
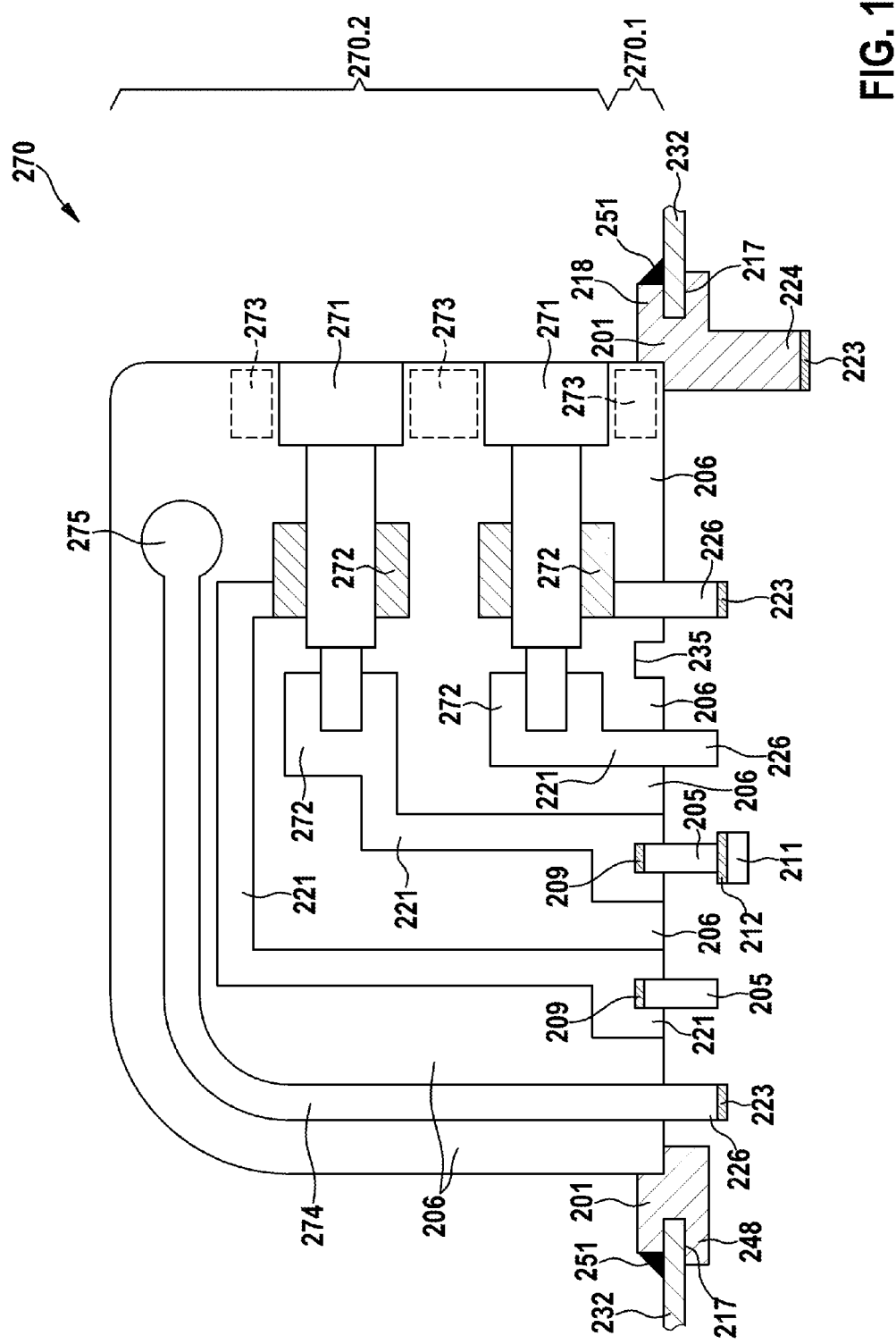
FIG. 1 shows a schematic cross-sectional view of a first exemplary embodiment of a connecting device in accordance with the present invention.

FIG. 1 shows a first exemplary embodiment of a cermet connecting device 270 with two integrated connecting sockets 271 for receiving a connecting piece of the electrode lines, a peripheral cermet flange 201 for connection to an implant housing 232, and an integrated cermet rod antenna 274. Complex structures of this type are advantageously produced by means of the above-described multi-layer technique. The connecting device 270 comprises a feedthrough 270.1 in the lower portion in FIG. 1 and a header 270.2 in the upper portion illustrated in FIG. 1. The feedthrough 270.1 and header 270.2 are formed in one piece.

The integrated connecting sockets 271 constitute shaped openings in the supporting body of the connecting device 270, said supporting body being made of insulating material, preferably ceramic (referred to hereinafter as insulation ceramic), and form electrical contact points 272 for electrode plug connectors. The electrical (cermet) contact points 272 may be formed peripherally in the lateral surfaces of the connecting sockets 271 (contiguous regions protruding from the plane of the figures are indicated in the figures as hatched areas) or may take up partial regions thereof, and may be formed convexly or in a recessed manner with respect to the insulation ceramic 206. Some or all electrical contact points may also be formed by solid metal inserts, which are connected to the respective cermet pathway 221, or from cermet phases of a different composition, in particular, a different metal concentration, compared to the other portions of the cermet pathway 221 of the connecting device 270. With use of the above-described multi-layer technology, these solid metal inserts are likewise positioned as desired, preferably in the green compact phase during the course of the arrangement of the various layers, and are then sintered simultaneously.

In the exemplary embodiment illustrated in FIG. 1, the connecting socket 271 has a first contact point 272 in the proximal region of smaller diameter and a second contact point 272 in the further distally arranged region of larger diameter. In particular, the second contact point 272 is annular. The first contact point 272 can be referred to as being U-shaped or pot-shaped. The connecting socket illustrated in FIG. 1 is therefore used to receive a two-pin connecting piece of an electrode line. Two or more than two annular insulated second contact points spaced apart from one another may be provided in such a connecting socket 271 for the connection of electrode lines having three-pin connecting pieces or connecting pieces having more than three pins. To this end, the extent of the connecting socket 271 in the direction of its longitudinal axis and therefore of the connecting device 270 has to be increased as necessary.

To increase mechanical stability and to avoid blow-outs, it may be advantageous if cermet stabilizations or regions 273 of a different material composition (with a different MgO, $ZrO_2$ or glass concentration) are integrated at the entry points of the connecting sockets 271 or in other regions, said stabilizations otherwise having no relevant electrical functions or influences.

(Multi-layer) cermet pathways 221 proceed from the electrical contact points 272, are guided along in the connecting device 270 in an L-shaped manner and exit in the implant interior of the connecting device as electrical contact points, either in the form of cermet pins 226 or as metal solid pins 205, which are electrically and mechanically fixedly connected to the cermet pathways 221 via a hard solder 209. Alternatively, the cermet pathways 221 terminate in a planar manner with the surrounding insulation ceramic 206 (not illustrated in FIG. 1). The described cermet exit points in the form of cermet pins 226 or planar cermet terminations 221 may be provided fully or in part with electrical (hard solder) connecting points 223 (also called contact pads) so as to enable simplified and compact electrically/mechanically fixed (soft solder) connections to an electronic substrate or flexstrip or an EMI filter 257. The pins 205 or the cermet pins 226 may optionally be provided with (soft solderable) pads 211, which may be connected via a hard solder 212 or welded joints or other connection technologies.

To increase the electrical insulation resistance and to increase the electric strength in high-voltage applications, ceramic grooves 235 may be integrated between the electrical exit points 226, 205 or 221 in the insulation ceramic 206. Alternatively, ceramic lips that protrude beyond the surrounding insulation ceramic 206 (not illustrated) may be provided for the same purpose instead of ceramic grooves 235.

A preferably L-shaped antenna 274 that is designed either as cermet 221 or may consist of a solid (ductile) metal, a metal alloy, or, for improved high-frequency properties, a wire, strip, or the like coated with an electrically highly conductive metal, such as, for example, silver, may be integrated into the connecting device 270. The antenna 274 is advantageously separate from the external environment of the connecting device 270 or the electrical implant in a hermetically sealed manner, such that the antenna 274 does not necessarily have to consist of a biocompatible (cermet) material. The antenna 274, preferably formed as a rod antenna, may have at one of its ends a thickening 275, which increases and reduces the bandwidth capacity for transmitting and receiving frequencies and reduces the necessary antenna length. The rod antenna 274 may be U-shaped for example or may have a flat cross-section as well as further passive members surrounding it (not illustrated in this case) so as to achieve improved directional independence and an improved antenna gain. As with the other signal lines, the antenna 274 may also terminate in a planar manner on the inner side of the implant with the electrical insulation ceramic 206 (not illustrated in this instance) surrounding said antenna, may protrude as a cermet pin 226, or may be welded on in the form of a solid ductile pin, for example, via a hard solder (not illustrated in FIG. 1). A (soft-solderable hard solder) connecting point 223 may additionally be provided as a connection aid. For improved impedance matching of the antenna to the HF transmitter in the electrical implant or for input of the HF receiver in the electrical implant, the antenna 274 advantageously has no sharp kinks or changes in direction over its extent and has no sudden relatively large changes in cross section.

The connecting device 270 according to the present invention also has a peripheral flange 201, which, as illustrated in FIG. 1, is integrated in a hermetically sealed cermet design, such that an implant housing 232 is joined to the connecting device 270 via the flange 201, for example, by means of hermetically tight welded joints 251.

A solid ductile flange may also be provided instead of a cermet flange, wherein the insulation ceramic 206 of the connecting device 270 may be provided with a (metal) coating, such that a hard solder connects the flange 201 with the insulation ceramic 206 to the insulation ceramic 206 via the coating. The flange 201 may have a (cermet) welded protective lip 248, such that a gap 217 forms, into which the implant housing 232 is inserted and no components in the interior of the implant are damaged during welding in the region of the welded joints 251. In the embodiment illustrated in FIG. 1, the cermet flange 201 has an integrated cermet ground pin 224, which may additionally have a connection point or a contact pad 223 (for example, made of platinum) with connected hard solder (for example, made of silver) to facilitate the connection. In a variant, a ground pin may be connected to the (cermet) flange via a hard solder connection (see FIG. 3) or may be electrically and mechanically fixedly connected to the flange via a welded point (not illustrated in FIG. 1). In a further variant (not illustrated), a (soft-solderable) pad may be connected at the end of the ground pin to the (cermet) ground pin 224 via a hard solder.

Figure 2:
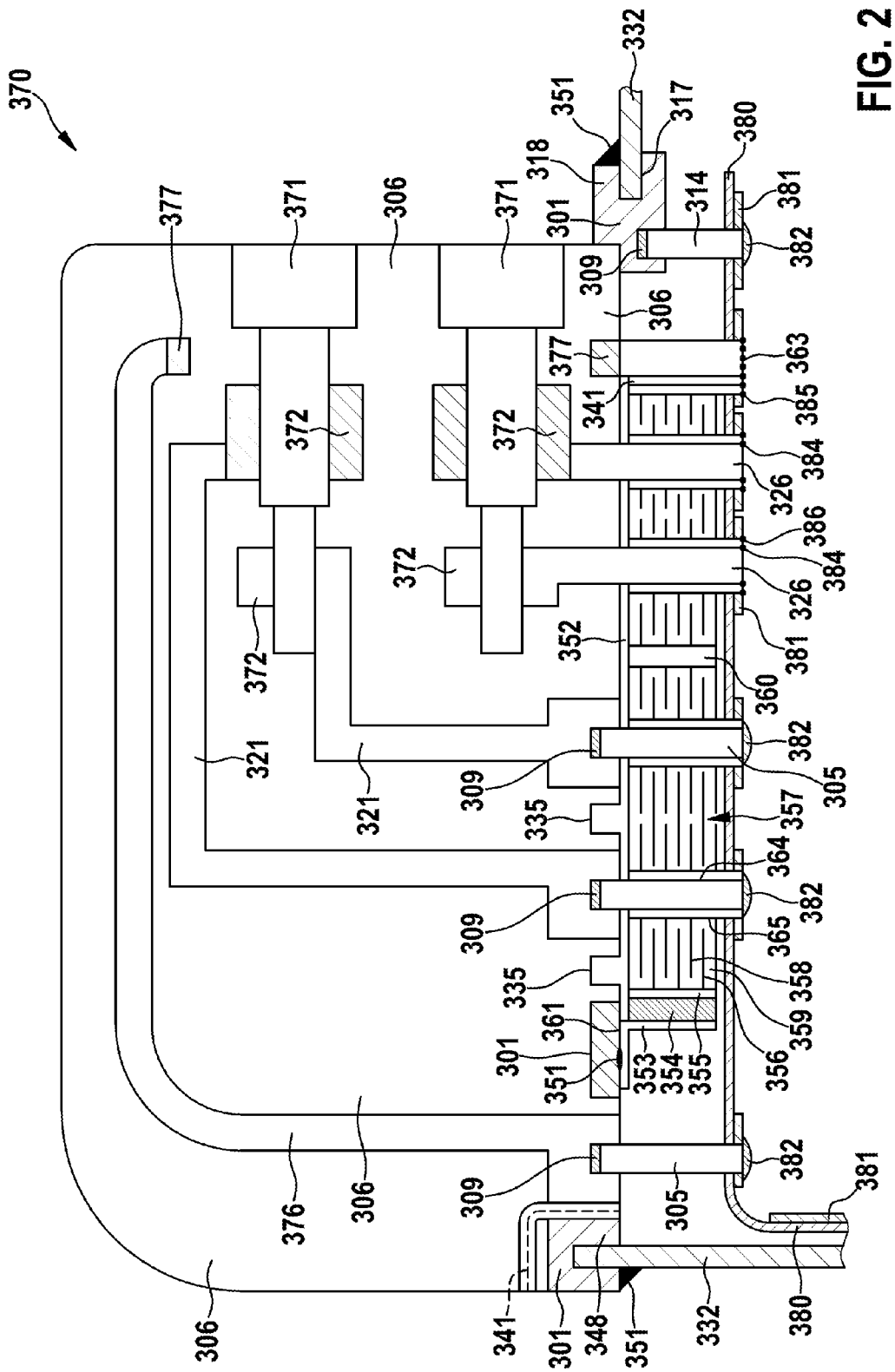
FIG. 2 shows a schematic cross-sectional view of a second exemplary embodiment of a connecting device in accordance with the present invention.

Compared to the first exemplary embodiment illustrated in FIG. 1, the second exemplary embodiment of a connecting device 370 illustrated in FIG. 2 additionally has an electromagnetic high-frequency filter (EMI filter) 357, which is connected to the connecting device 370 so as to block high-frequency electromagnetic interfering radiation. Apart from the EMI filter 357 and the loop antenna 376 illustrated in this instance, the connecting device 370 corresponds to the connecting device in FIG. 1, wherein, in this exemplary embodiment and the following exemplary embodiments, the reference signs corresponding to one another have a different number 3, 4, etc. instead of the first number 2 (indicating the hundred numeral). For example, the connecting socket in FIG. 1 is provided with reference sign 271, whereas it is denoted in FIG. 2 by reference sign 371 and in FIG. 3 by reference sign 471, and so on.

The EMI filter effect at the electrical implant is produced by means of a low-pass filter, a filter component of said low-pass filter being constituted by the feedthrough capacitors at the feedthrough. The feedthrough capacitors in the EMI filter 357 are formed in this case from the signal-guiding capacitor plates 358, the dielectrics 359 and the ground capacitor plates 356. Filter signal areas 365 form electrical access points to the signal capacitor plates 358, and filter ground areas 355 form access points to the ground capacitor plates 356.

As illustrated in this exemplary embodiment, the pins 305 can advantageously be electrically and mechanically reliably connected to the filter signal areas 365 via soft solder 364. Other connection forms, such as electrically conductive adhesive bonding, welding, and clamping are also conceivable however in other embodiments. The pins 305 are expediently connected in an electromagnetically HF-tight manner over their entire lateral periphery via the soft solder 364.

In the embodiment illustrated in FIG. 2 the cermet flange 301 has an enlarged cermet phase 341, which can advantageously be soft soldered and on which electrically mechanically stable connections to the filter ground areas 355 can be produced by means of a soft solder 363. In this case too, further connection forms (not illustrated), such as, for example, electrically conductive adhesive bonding, and clamping are conceivable. The connection 363 to the cermet phase 341 is produced in an electromagnetically HF-tight manner over minimal distances and over the entire periphery of the EMI filter 357, where possible.

In an embodiment illustrated alternatively in FIG. 2, the soft solder 354 is provided with a ductile, metal sleeve 353 that can be soft soldered and that is electrically and mechanically connected to the flange 301 via a plurality of welded points 351. An electromagnetically HF-tight connection between the filter ground areas 355 and the flange 301 is thus produced via this sleeve 353 and the soft solder 354 as reference potential if the sleeve 353 is connected over at least a large part of its total periphery to the EMI filter 357. The connection between the filter ground areas 355 and the sleeve 353 can be produced in different, further connection forms (not illustrated in this instance), such as electrically conductive adhesive bonding, welding or clamping.

Due to the connection of EMI filters 357 to the connecting device 370, it is possible that the connecting device 370 may become damaged and may lose its hermeticity between the interior and exterior of the implant. A continuous space 352 between the surface of the connecting device 370 and the EMI filter 357 is used to demonstrate the intact hermeticity of the connecting device 370 on the entire inner side of the implant by means of helium gas. The necessary helium gas access point to the space 352 is produced from the outside in this exemplary embodiment by means of an opening 360 in the EMI filter 357 or by openings between the sleeve 353 and the flange 301.

In FIG. 2, an electronic substrate or flexstrip 380 is also illustrated, which has integrated electrical conductor paths 381 so that the electrical signals are guided from and to the signal lines 321, 305 or 314 of the connecting device 370 or 365 of the EMI filter 357. The electrical and mechanical connection of these signal lines to those of the flexstrip 380 can be produced in the exemplary embodiment illustrated in FIG. 2 via soft solder connections 382 and, alternatively, via welded joints 383 between the cermet pathway 326 and conductor path 381, via welded joints 384 between the cermet pathway 326 and the signal line 365 of the EMI filter 357, via a welded joint 385 between the cermet pathway 326 and the ground line 355 of the EMI filter 357, and/or via a welded joint 386 between the conductor path 381 and the signal line 365 of the EMI filter 357.

In further variants (not illustrated), these electrical-mechanical connections can be produced by means of further connection forms, such as, for example, electrically conductive adhesive bonding, welding, or clamping. As illustrated in this embodiment, the flexstrip 380 may have a curved extent, for example, so as to enable mechanical decoupling from the electronic substrate connected to said flexstrip and to save space.

In contrast to FIG. 1, the ground pin 314 in this variant is connected, for example, via a hard solder connection 309 to the (cermet) flange 301. In contrast to the first exemplary embodiment of the connecting device 370 according to the present invention, the flange 301 is also connected to the insulation ceramic 306 via a plurality of cermet phases 341 so as to avoid mechanical stress peaks and to achieve greater mechanical load-bearing capacities.

As illustrated in FIG. 2, the implant housing 332 can be connected in a plurality of directions to the flange 301 of the connecting device 370.

In an embodiment (not illustrated), an EMI filter can be replaced by a plurality of capacitors (advantageously SMD ceramic capacitors), wherein these capacitors are electrically connected over the conductor paths 381 of the flexstrip 380 in the close vicinity of the signal lines 321, 305, 326 or 314 of the connecting device 370 and take on the filtering effect of the EMI filter.

In an exemplary embodiment (not illustrated), the EMI filter can be integrated directly into the connecting device 370.

Figure 3:
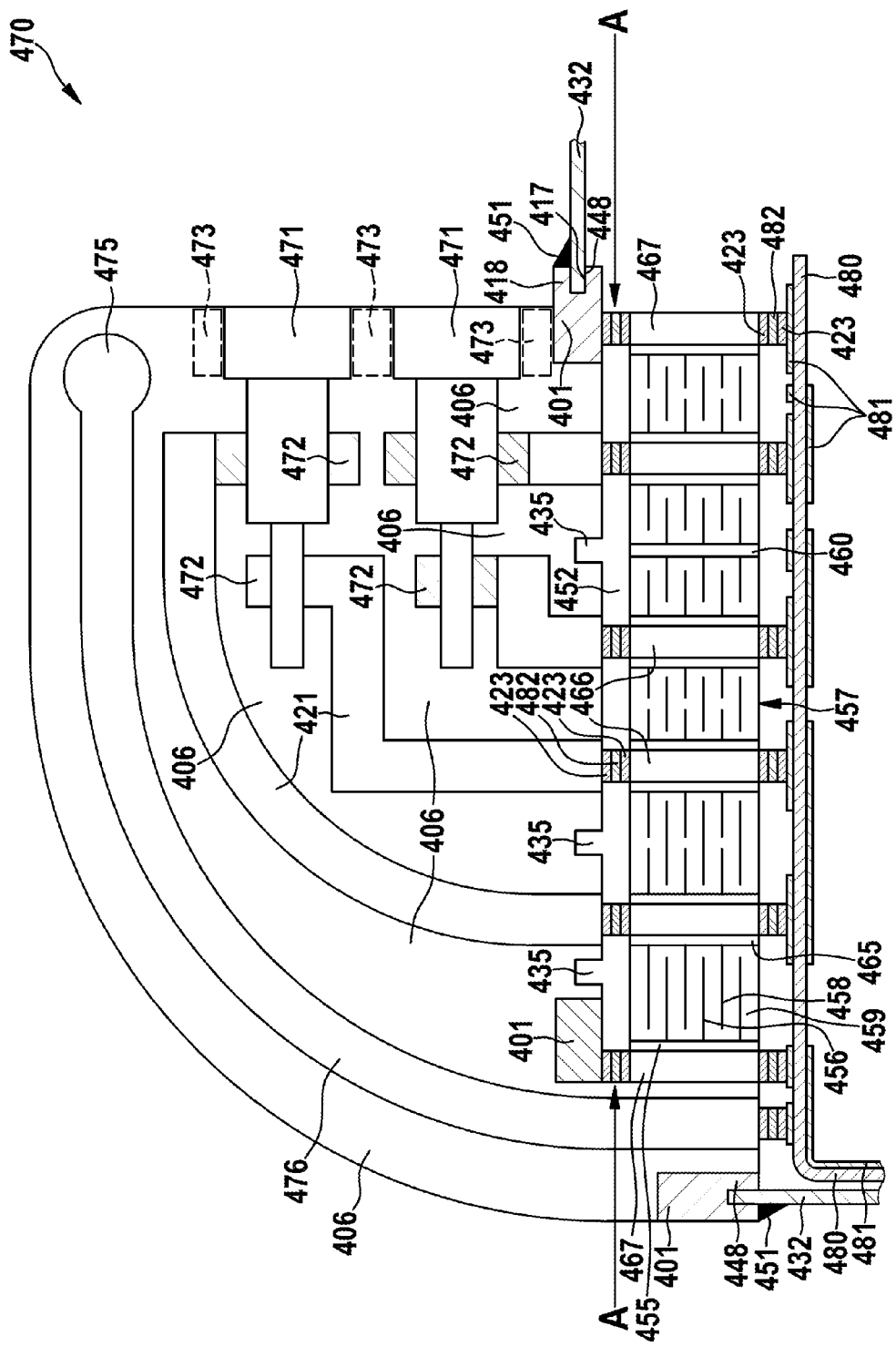
FIG. 3 shows a schematic cross-sectional view of a third exemplary embodiment of a connecting device in accordance with the present invention.

FIG. 3 shows a third exemplary embodiment of a connecting device 470, which corresponds substantially in terms of design to the connecting devices 270, 370 illustrated in FIGS. 1 and 2, but in this exemplary embodiment of FIG. 3 the electromagnetic high-frequency filter (EMI filter) 457 and the other connection points are connected uniformly via (hard solder) connection points 423 and via soft soldered joints 482 to the connecting device 470 and to the electronic substrate or flexstrip 480 so as to block high-frequency electromagnetic interfering radiation in a compact design.

In this exemplary embodiment, the cermet pathways 421 of the cermet connecting device 470 terminate flush with the electrical insulation ceramic 406 surrounding them. The pathways 421 are also each provided with soft solderable hard solder connection points 423 or contact pads at their exit surfaces.

Figure 5:
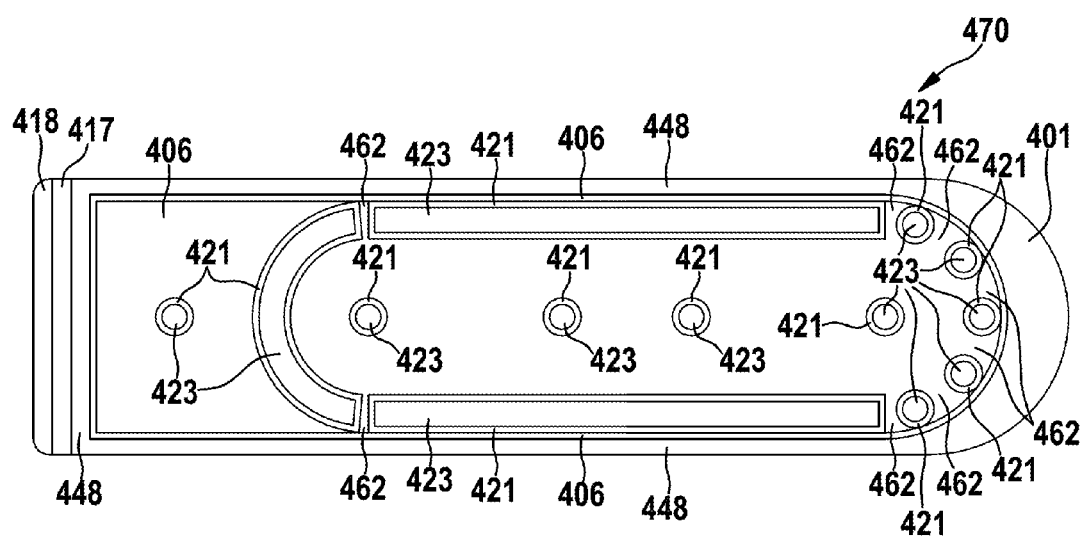
FIG. 5 shows a schematic plan view of the connecting device of the exemplary embodiment according to FIG. 3 from a plane along line A-A (see FIG. 3)

The EMI filter 457 has signal lines 466, which are electrically and mechanically fixedly connected to the respective coatings of the signal areas 465 of the EMI filter 457. The EMI filter 457 additionally has ground lines or peripheral ground areas 467, which provide a possibility for connection for the reference or ground potential. The ground lines or peripheral ground areas 467 are electrically and mechanically fixedly connected to the coatings of the ground areas 454 of the EMI filter 457. In this exemplary embodiment, both the ground lines or peripheral ground areas 467 and the signal lines 466 terminate flush with the end faces of the EMI filter 457 so as to achieve the most compact design possible. Where possible, the ground lines or peripheral ground areas 467 of the EMI filter 457 are electrically connected over the entire periphery and over minimal distances to the cermet flange 401 and to the ground lines of the electronic substrate or flexstrip 480 so as to achieve the most complete possible EMI filter effect. Small gaps 462, which are used to examine the hermeticity of the connecting device 470 in the space 452 and which are illustrated in FIG. 5, only influence the EMI filter effect of the structure to an insignificant extent.

In an exemplary embodiment (not illustrated), the electrical cermet pathways may be either raised or recessed compared to the electrical insulation ceramic 406 surrounding them. The same is true for the electrical signal lines 466, the ground lines and the peripheral ground areas 467 of the EMI filter 457. For example, the protruding electrical pathways of the EMI filter 457 may engage in notches, which are arranged opposite, are formed by recessed pathways and, vice versa, thus facilitate the process of joining the connecting device 470 to the EMI filter 457.

A comparable arrangement of an EMI filter 457 with similar advantages can also be achieved with a (cermet) feedthrough instead of with a connecting device 470.

Figure 4:
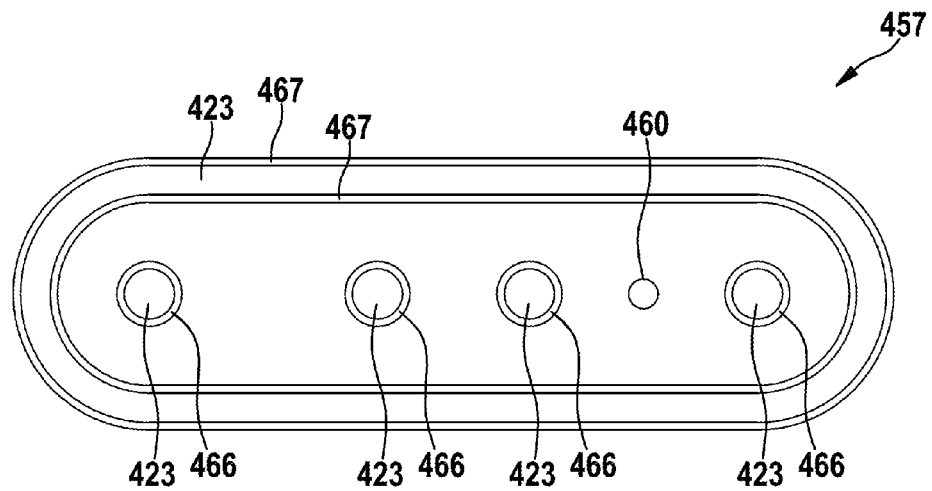
FIG. 4 shows a schematic plan view of the EMI filter of the exemplary embodiment according to FIG. 3 from a plane along line A-A (see FIG. 3)

FIG. 4 shows a plan view of the EMI filter 457 of FIG. 3 along the line A-A. The electrical signal lines 466 and the ground lines or peripheral ground areas 467 of the EMI filter 457 can be seen. These electrical connection points are optionally provided with (hard solder) connection points 423, which facilitate the further electrical connection, for example, by means of soft soldering. The electrical connection points may have any desired form, and not only the circular form as indicated in FIG. 4. A ventilation bore 460 is additionally indicated schematically through the EMI filter 457 in order to examine the hermeticity.

The connecting device 470 from FIG. 3 is illustrated in plan view in FIG. 5, as viewed from the space 452. At least one gap 462 between the electrical pathways 421 ensures that there is access for helium gas into the space 452 between the EMI filter 457 and the connecting device 470, so that possible damage to the connecting device 470 can be detected that may have been produced once the EMI filter 457 has been joined to the connecting device 470 and that may impair the seal. The electrical connection points 421 are optionally provided with (hard solder) connection points 423, which facilitate the further electrical connection, for example, by means of soft soldering. The electrical connection points 421 may have any desired form, and not just the circular form as indicated in FIG. 5. The arrangement of the electrical connection points 421 or of the (hard solder) connection points 423 is selected such that a compact and reliable electrical and mechanical connection to the EMI filter 457 or to the electronic substrate or flexstrip 480 is enabled.

Figure 6:
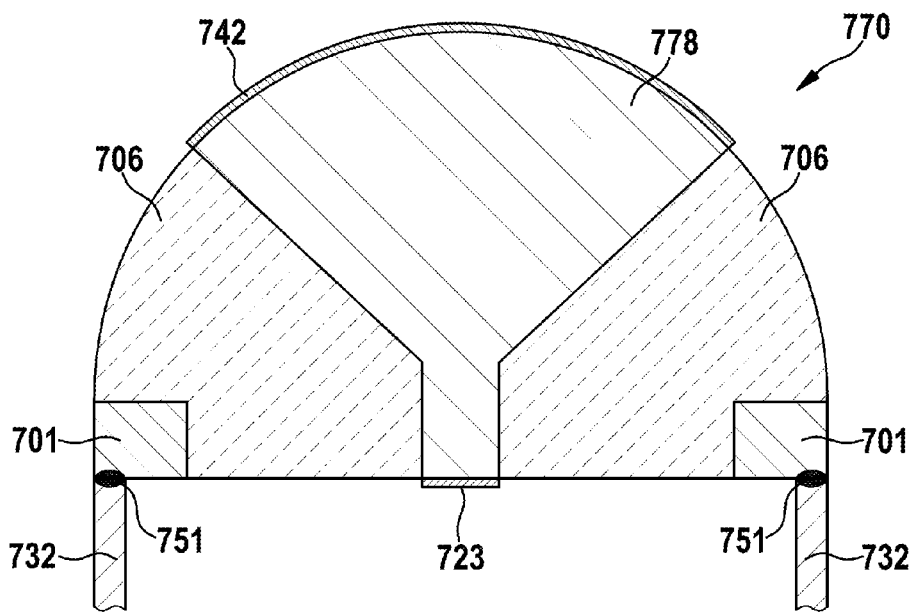
FIG. 6 shows a cross-sectional view of a connecting housing for a "leadless pacemaker"

FIG. 6 shows an example of a connecting device 770 in the form of a schematic full section view, which has at least one cermet electrode 778 integrated instead of a socket 471 (as in FIG. 3). The entire arrangement formed of the cermet electrode 778, the electrical insulation 706 surrounding said electrode, the (cermet) flange 701 and the implant housing 732 connected via the welded joint 751 advantageously provide the smoothest outer surface possible with few points of contact, such that injury to the patient is avoided or otherwise minimized. The cermet electrode 778 may optionally advantageously be provided with a fractal-like coating 742, which considerably reduces the electrical junction impedance between the electrode 778 and the surrounding tissue of the patient (normally the inner wall of a myocardial muscle), such that electrical stimulation impulses can be recorded by the electrical implant with lower electrical losses and electrical action potential (normally of the myocardial muscle cells) with fewer falsifications, such that the algorithms for successful treatment of the heart can be provided more reliably alongside improved actions.

In the interior of the implant, the at least one cermet electrode may have a (hard solder) connection point 723 or a contact pad for a facilitated mechanically and electrically stable connection to an electronic substrate or a flexstrip. In an exemplary embodiment (not illustrated), special shapings can be integrated in the connecting device that are used to ensure reliable anchoring of the connecting device in the patient's tissue.

Figure 7:
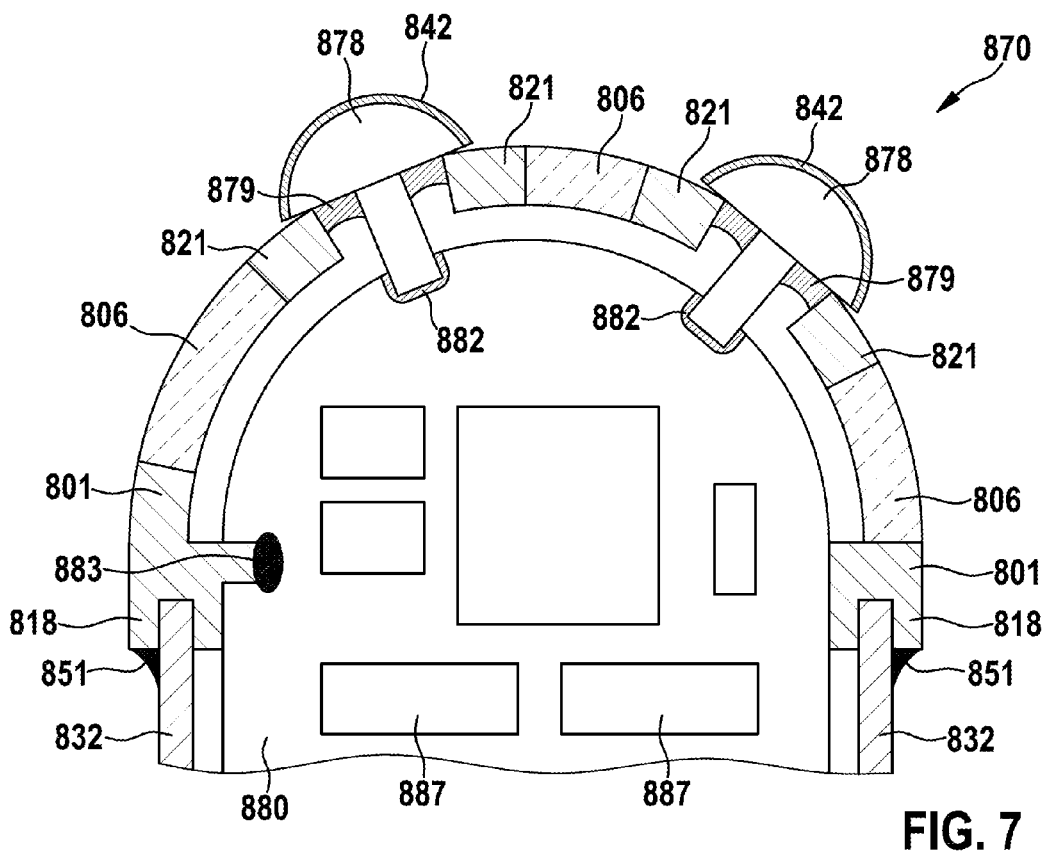
FIG. 7 shows a cross-sectional view of a further connecting housing for a "leadless pacemaker"

FIG. 7 shows an example of a connecting device 870 similar to FIG. 6, but in this case the electrodes 878 consist of solid metal, such as, for example, iridium Ir, tantalum Ta, niobium Nb, titanium Ti, platinum Pt or other biocompatible materials or alloys thereof. In this exemplary embodiment, the electrodes are connected in a mechanically fixed and hermetically tight manner to cermet phases 821 of the connecting device 870 by means of a hard solder 879 that is as biocompatible as possible, such as, for example, gold (Au), or is sintered directly into the cermet phases 821 without hard solder 879.

The electrodes 878 may optionally protrude beyond their surrounding environment and may likewise be provided with a fractal-like coating 842. By way of example, an electrical soft solder connection 882 between the electrodes 878 and an electronic substrate 880, which is provided with electronic components 887, such as, for example, resistors, capacitors, diodes, electronic chips, advantageously in SMD design, is illustrated. A welded joint 883 between the cermet ground pin 824 of the flange 801 and the electronic substrate 880 is also illustrated by way of example.

Figure 8:
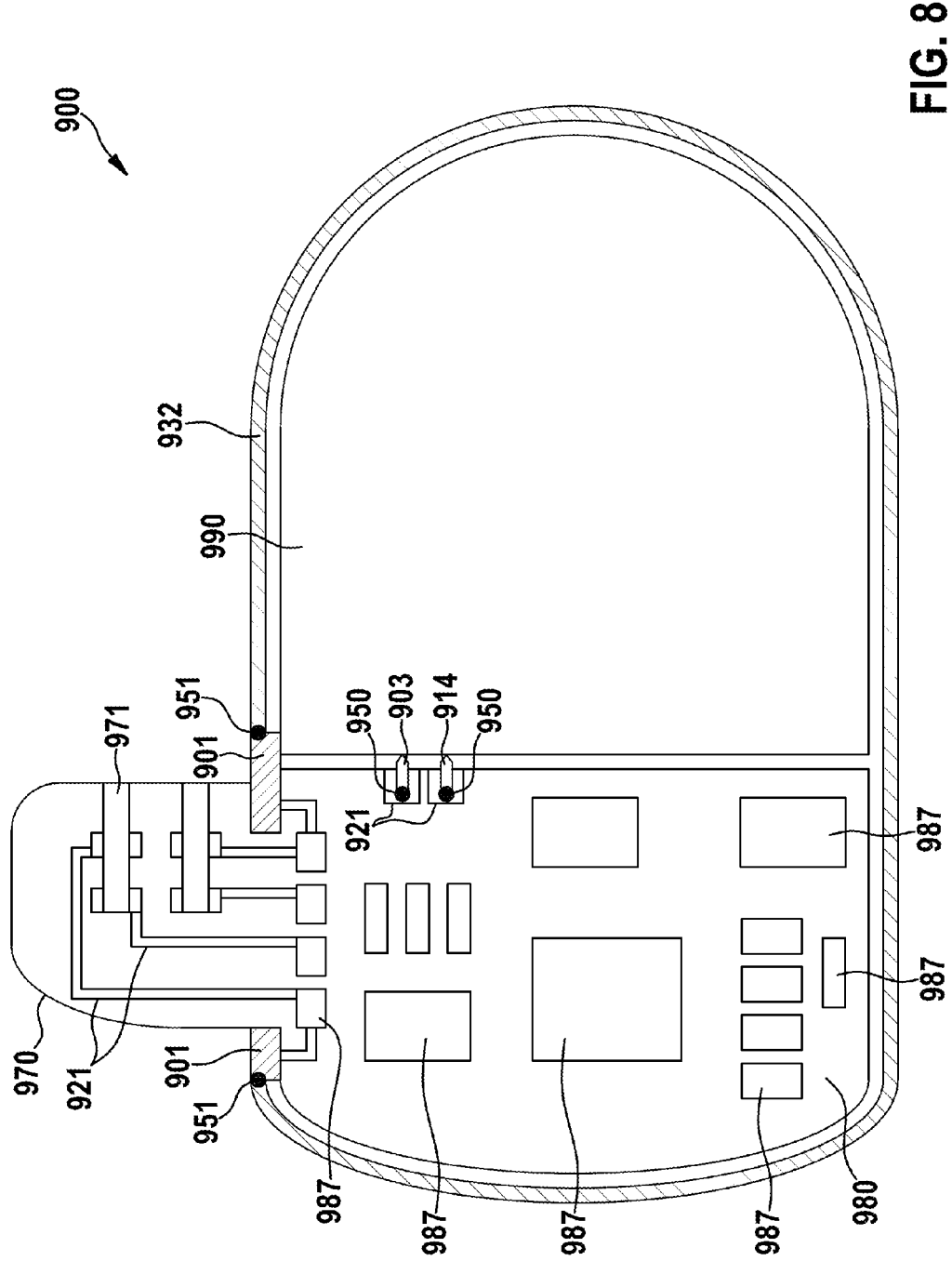
FIG. 8 shows a longitudinal sectional view of an electromedical implant according to the present invention.

An exemplary embodiment of an electromedical implant 900 with a connecting device 970 is illustrated in FIG. 8 similarly to FIGS. 2-5, wherein a cermet ceramic substrate 980 is additionally formed in one piece with the connecting device 970, such that there is no need for an additional joining process between the connecting device 970 and the substrate 980.

The substrate 980 is advantageously constructed in multilayer form, such that intersecting cermet pathways are separated spatially from one another and are electrically insulated. The electronic components 987 are advantageously electrically and mechanically reliably contacted, for example, by means of reflow soldering via the soft solder 982 and corresponding (soft-solderable hard solder) connection points 923 at the cermet pathways 921. The cermet phases 921 are directly soft-solderable without explicit hard solder connection points 923 if they consist, for example, of platinum Pt, iridium Ir or alloys thereof, or other soft-solderable metal alloys.

A peripheral flange 901 is integrated in the connecting device 970 and is mechanically and electrically fixedly connected in a hermetically tight manner to the housing 932 of the electrical implant 900 via welded points 951.

At the transition to the connected substrate 980, the connecting device 970 optionally has filter capacitors 987, which are each soft soldered on between the cermet pathways 921, starting from the cermet sockets 971, and the cermet pathways 921, starting from the flange 901, such that an EMI filter function is produced, which produces the electromagnetic interfering radiation coupled in via the electrode lines and the cermet sockets 971.

A battery 990, which is integrated in the electrical implant 900 and which supplies electrical energy to the electronics on the substrate 980, is additionally illustrated. In this exemplary embodiment, a voltage-carrying pin 903 and a ground pin 914 start from the battery 990 and are electrically connected by weld points 950 to cermet phases of the electronic module 980.

An electrically conductive cermet, for example, with platinum as can be used for the above-described connecting devices, preferably consists approximately 40% by volume to 50% by volume of Pt, and of $Al_2O_3$ for the rest.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE CHARACTERS 201 flange
205, 305 pin
206, 306, 406 insulation ceramic
209, 309, 409 hard solder
211 pad
212 hard solder
314, 914 ground pin
217 peripheral groove in the flange 201
218, 818 welded lip on the flange 201
221, 321, 326, 421, 821, 921 cermet pathway
223, 423, 723 hard solder connection point (soft-solderable)
224 cermet ground pin
226 cermet pin
232, 332, 432, 732, 832, 932 implant housing
235, 335, 435 ceramic groove
251, 351, 451, 951 weld point
252, 352, 425 space
270, 370, 470, 770, 870, 970 cermet connecting device
270.1 feedthrough portion of the cermet connecting device
270.2 header portion of the cermet connecting device
271, 371, 471, 971 socket in the cermet connecting device
272, 372, 472 electrical (cermet) contact point
273 cermet stabilization
274 (cermet) rod antenna
275 thickened end of the (cermet) rod antenna 274
341 cermet phase
353 sleeve
354 soldered joint of the sleeve 353
355, 455 coating of the ground area
356, 456 ground capacitor plate
357, 457 EMI filter
358, 458 signal capacitor plate
359, 459 dielectric
360, 460 ventilation bore
361 opening at the sleeve 353
363, 364 soldered joint
365, 465 coating of the signal area
376, 476 (cermet) loop antenna
380, 480, 880, 980 electronic substrate or flexstrip
384, 385, 386 weld point
462 gap (space)
467 ground line of the EMI filter
481 electronic pathway
742 cermet coating
778, 878 electrode
879 hard solder
882 soft solder
883 weld point
887, 987 electronic component (for example SMD) capacitor, (SMD), resistor, chip, etc.
900 electromedical implant
990 battery

We claim:

1. A connecting device for an electromedical implant having a housing, the connecting device comprising:
    a feedthrough and a header, wherein the feedthrough and the header are formed in one piece,
    wherein the connecting device has a supporting body made of insulating material as well as at least one electrically conductive pathway, which, at a first end and/or at a second end, has at least one contact point for transferring electrical signals between a circuit arranged in the housing and an electrode line, wherein the pathway contains a cermet material.

2. The connecting device as claimed in claim 1, wherein the feedthrough forms a first portion of the connecting device and the header forms a second portion of the connecting device, wherein the first portion hermetically seals the housing.

3. The connecting device as claimed in claim 1, wherein a contact pin, a contact pad or a first socket is formed in the supporting body at the first end of the at least one pathway, and a second socket is formed in the supporting body at the second end of the respective pathway and is used to plug in a corresponding connecting piece of the electrode line.

4. The connecting device as claimed in claim 1, wherein the first end and/or the second end of the at least one pathway is/are designed in the form of at least one hollow cylinder casing portion or a hollow cylinder casing or a flange portion, wherein the inner face of the hollow cylinder casing portion or of the hollow cylinder casing or of the flange portion of the at least one pathway is used as a contact point of the respective first or second socket.

5. The connecting device as claimed in claim 1, wherein the material of the at least one pathway at the first end and/or the second end of the at least one pathway is different from the material of the at least one pathway in an intermediate portion, and has a greater concentration of metals and/or metal alloys than in the intermediate portion, and is composed of at least one metal or a metal alloy.

6. The connecting device as claimed in claim 1, wherein in an entry region of a socket, the supporting body has a volume area that contains a cermet material.

7. The connecting device as claimed claim 1, wherein an antenna containing a cermet material and having a thickening at one of its ends is arranged in the supporting body.

8. The connecting device as claimed in claim 1, further comprising a peripheral flange which contains a cermet material.

9. The connecting device as claimed in claim 1, further comprising an EMI filter or, in the region of the first end of the at least one pathway, the connecting device is connected to an EMI filter.

10. The connecting device as claimed in claim 1, characterized in that the at least one pathway in an intermediate portion has a region that is L-shaped.

11. The connecting device as claimed in claim 1, wherein the connecting device is produced or producible by means of multi-layer technology.

12. An electromedical implant comprising: a housing, a battery, an electric circuit and a connecting device as claimed in claim 1, wherein the electric circuit and the connecting device are formed in one piece and the connecting device hermetically seals the housing of the medical implant.

13. A connecting device for an electromedical implant having a housing, the connecting device comprising:
   a feedthrough and a header, wherein the feedthrough and the header are formed in one piece; and
   a peripheral flange which contains a cermet material.

14. The connecting device as claimed in claim 13, further comprising an EMI filter or, in the region of the first end of the at least one pathway, the connecting device is connected to an EMI filter.

15. The connecting device as claimed in claim 13, wherein the connecting device is produced or producible by means of multi-layer technology.

16. An electromedical implant comprising: a housing, a battery, an electric circuit and a connecting device as claimed in claim 13, wherein the electric circuit and the connecting device are formed in one piece and the connecting device hermetically seals the housing of the medical implant.

17. A connecting device for an electromedical implant having a housing, the connecting device comprising:
   a feedthrough and a header, wherein the feedthrough and the header are formed in one piece,
   wherein the connecting device is produced or producible by means of multi-layer technology.

18. The connecting device as claimed in claim 17, wherein the feedthrough forms a first portion of the connecting device and the header forms a second portion of the connecting device, wherein the first portion hermetically seals the housing.

19. The connecting device as claimed in claim 17, further comprising an EMI filter or, in the region of the first end of the at least one pathway, the connecting device is connected to an EMI filter.

20. An electromedical implant comprising: a housing, a battery, an electric circuit and a connecting device as claimed in claim 17, wherein the electric circuit and the connecting device are formed in one piece and the connecting device hermetically seals the housing of the medical implant.

* * * * *